United States Patent
Kang et al.

(10) Patent No.: US 6,563,903 B2
(45) Date of Patent: May 13, 2003

(54) CONTAINER INSPECTION APPARATUS

(75) Inventors: Kejun Kang, Beijing (CN); Wenhuan Gao, Beijing (CN); Yinong Liu, Beijing (CN); Zhiqiang Chen, Beijing (CN); Yuanjing Li, Beijing (CN); Jianmin Li, Beijing (CN); Chuanxiang Tang, Beijing (CN); Junli Li, Beijing (CN); Huayi Zhang, Beijing (CN); Wanlong Wu, Beijing (CN); Zhizhong Liang, Beijing (CN); Dong Yun, Beijing (CN); Ou Sun, Beijing (CN); Jianjun Su, Beijing (CN); Shangmin Sun, Beijing (CN)

(73) Assignees: Tsinghua University, Beijing (CN); Nuctech Company Limited, Beijing (CN)

( * ) Notice: Subject to any disclaimer, the term of this patent is extended or adjusted under 35 U.S.C. 154(b) by 0 days.

(21) Appl. No.: 09/889,998
(22) PCT Filed: Feb. 28, 2001
(86) PCT No.: PCT/CN01/00313
§ 371 (c)(1),
(2), (4) Date: Jul. 23, 2001
(87) PCT Pub. No.: WO01/65245
PCT Pub. Date: Sep. 7, 2001

(65) Prior Publication Data
US 2002/0136353 A1 Sep. 26, 2002

(30) Foreign Application Priority Data
Mar. 1, 2000 (CN) .......................... 00103342 A

(51) Int. Cl.⁷ .............................................. G01N 23/04
(52) U.S. Cl. ........................................... 378/57; 378/55
(58) Field of Search ............................ 378/57, 53, 62, 378/58, 55

(56) References Cited

U.S. PATENT DOCUMENTS
5,097,494 A   3/1992   Pantelleria et al.
(List continued on next page.)

FOREIGN PATENT DOCUMENTS
CN   98101501.8   10/1998
CN   99215812.5   6/2000
(List continued on next page.)

Primary Examiner—Drew A. Dunn
Assistant Examiner—Irakli Kiknadze
(74) Attorney, Agent, or Firm—Rodman & Rodman

(57) ABSTRACT

A relocatable container inspection device, which is constituted by modularized units, is used for inspecting a container. The device comprises: a first cabin unit including a radiation source for generating a beam of penetration radiation for penetrating the container to be inspected; a second cabin unit including detectors for detecting the beam of penetration radiation penetrating through the container being inspected and producing corresponding radiographic signals, the second cabin unit and the first cabin unit being arranged oppositely in both sides of an inspection passage; a gantry unit bridging the first cabin unit and the second cabin unit to form a portal-shaped frame adapted for straddling the container being inspected; means for moving the frame relative to the container being inspected along the inspection passage, so that the detectors receive the beam of the penetration radiation generated from the radiation resource and passing through the container being inspected, thereby continuously scanning the container and producing the corresponding radiographic signals, wherein the first cabin unit, the second cabin unit and the gantry unit are all individually made as modular units so as to be quickly and easily assembled and disassembled with each other on the inspection site. In the present invention, all of the modularized units of the container inspection device can be easily assembled and disassembled in the work field, and the dimensions of each modular unit are sized to be suitable for road transports and to be facilitate for the device's movement.

10 Claims, 2 Drawing Sheets

Figure 1:
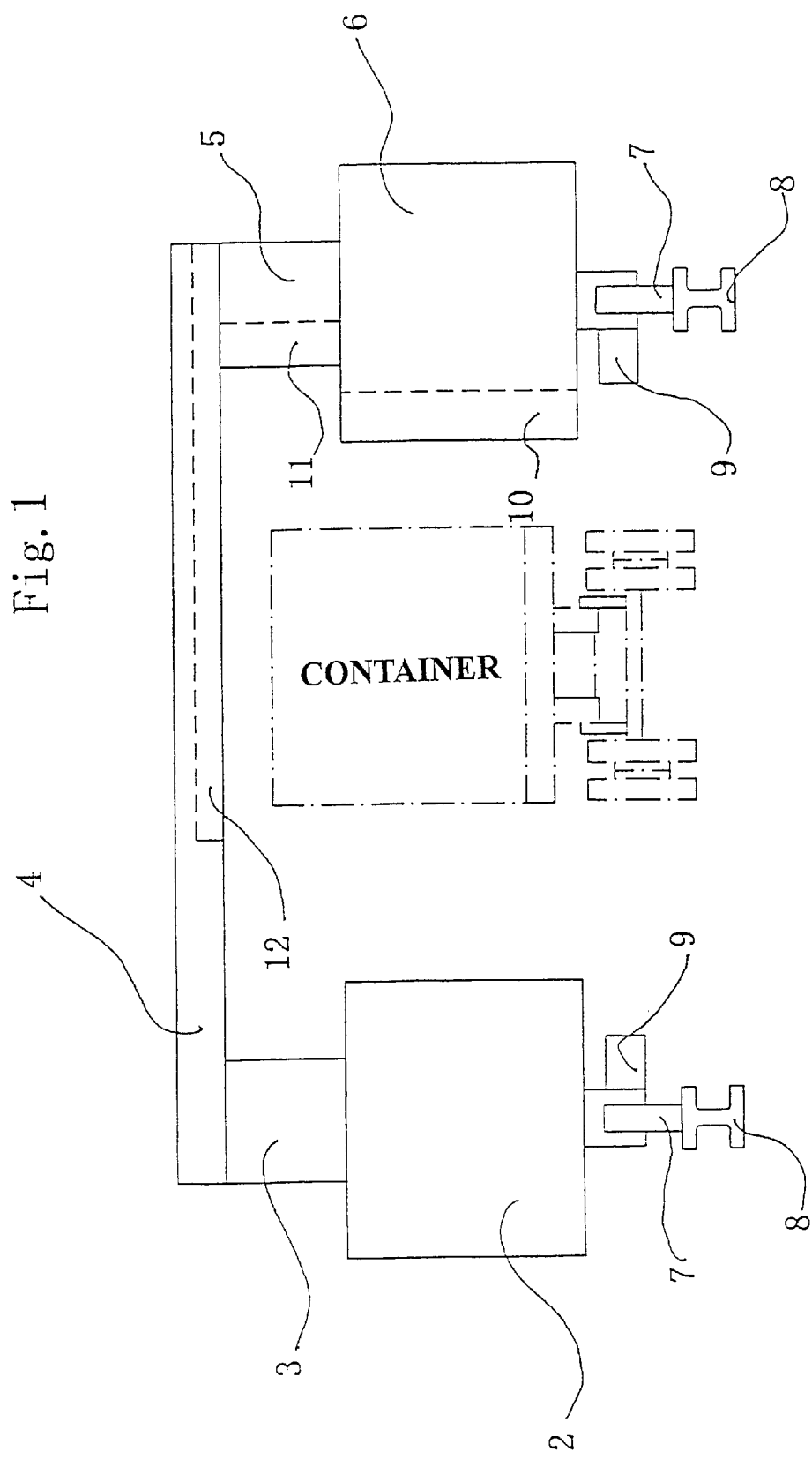

U.S. PATENT DOCUMENTS 5,692,028 A * 11/1997 Geus et al. .................. 378/57
5,838,759 A    11/1998 Armistead
6,058,158 A * 5/2000 Eiler .......................... 378/57
6,255,654 B1 * 7/2001 Verbinski et al. ........ 250/358.1

FOREIGN PATENT DOCUMENTS

CN    99253456.9    8/2000
CN    99256846.3    10/2000

* cited by examiner

CONTAINER INSPECTION APPARATUS

FIELD OF THE INVENTION

The present invention relates to a container inspection device, and more particularly relates to a relocatable container inspection device.

PRIOR ART

In the prior art, there have been proposed a kind of trailer-type container inspection device since 1990, such as those manufactured by Heimann Systems GmbH and British Aerospace PLC. This kind of device is installed in a fixed site, and a stationary radiation source for generating a high-energy X-ray and an array of detectors for receiving the X-ray of penetrating through the container being inspected are both arranged into an inspection hall with shield walls. A special conveying apparatus is employed so as to move the container to pass through an inspecting passage. By moving the container passing through the inspection passage, the detectors receive X-ray penetrating through the container, then the density distribution of the objects in the container is obtained according to signal intensity variations. Then, by transforming the data on the signal intensity to the data on the image gray levels, the radiographic image of the objects located in the container can be obtained. In this prior art, the accelerator of radiation source and the detector array are permanently installed, which ensures to get good radiographic image, to inspect lots of containers in a certain period, and to have a good operation condition for the inspection device so as to make the inspection device run in a security and reliability manner. However, this known inspection device has the following disadvantages: a huge space and area are needed to accommodate the device, the inspection passage is too long (at least 46.3 m), a set of huge and heavy pulling apparatus is needed, and once installed, the device has to be permanently located in the constructed site with a long construction period and high costs. In order to overcome these drawbacks, various mobile inspection systems have been developed.

Typically, there has been proposed a mobile inspection system in which all of the equipments relative to the radiation source, the detectors and the controlling units are mounted on a carrying vehicle. Despite the fact that the mobile inspection systems have some obvious advantages such as occupying a small area, being easy to use, and lowering the costs, there are also appeared many problems resulted from the vehicle's structure itself, for example, the quality of radiographic image is poor, less containers can be inspected in a certain time, the inspection range becomes smaller, the inspection capability is weaker, the reliability of the device is suffered for the reason that the device is easily influenced by environment condition, the device needs more maintains, the device is difficult to be adjusted during the installation, and the device may harm the environment in use.

U.S. Pat. No. 5,692,028 and U.S. Pat. No. 5,903,623 disclose some mobile X-ray inspection systems for large objects, in which the entire device is mounted on a vehicle, so as easily to be moved and conveyed. However, since the volume and the weight of the device can not be big and heavy enough respectively so as to meet the load capacity of the vehicle on which the inspection device mounted, it is impossible to take sufficient safety protection measures for protecting people from harmful beam generated from the radiation source (As can be understood, in order to take sufficient safety protection measures, enough protection materials will be used so that more space will be occupied and heavier load will be put on the carrying vehicle). For the purpose of ensuring the operator and surrounding people's personal security, it has to use a relative low intensity X-ray as radiation source, resulting in the radiographic image not so good, thus making the device inefficiency. Moreover, in this kind of the mobile inspection system, the operators have to work within the vehicle together with the device itself. That is to say, the operators have to work in a poor and narrow working space.

U.S. Pat. No. 5,638,420 discloses a straddle inspection system comprising a moveable frame, which can straddle the container being inspected. Although the frame is moveable, it is difficult for the straddle inspection system to be moved or conveyed for the dead weight and bulkiness of the frame, in addition, it is time and labour consuming to install the straddle inspection system in work site. Further, as the frame needs to be conveyed as an integral structure, the total weight of the frame cannot be designed to be too heavy, so that any heavier beam stop is prevented to be employed, thus the dosage and intensity of radiation source have to be limited. In consequence, the quality of the radiographic image is limited.

Besides, in U.S. Pat. No. 5,638,420, the operation room and controlling apparatus are mounted on the top of the straddle structure, forming a top-heavy but bottom-light frame structure. To be adapted for the containers with different sizes, the radiation source has to be lifted or lowered together with the telescoping legs. It is not easy to operate the straddle inspection system for its complicate structure.

OBJECT OF THE PRESENT INVENTION

The main object of the present invention is to provide a relocatable container inspection device, which is constituted by modularized units, and in which all of the units can be easily assembled and disassembled in the work field, and the dimensions of each modular unit are sized to be suitable for road transports, so that the device can be easily moved from one location to another.

Another object of the present invention is to provide a relocatable container inspection device, which has the advantages of both the fixed-site container inspection device and the mobile container inspection device, while can overcome the drawbacks of the two kinds of the container inspection devices in the prior art.

Another object of the present invention is to provide a relocatable container inspection device, which has a simple structure, is convenient to be operated, and is easy to be maintained.

Another object of the present invention is to provide a relocatable container inspection device, which can employ a high-energy X-ray source, so as to make the radiographic image more clear, thus the radiographic image can be more easily identified, in consequence, the container inspection efficiency is enhanced.

Another object of the present invention is to provide a relocatable container inspection device, which provides suitable working environment for the operators, so as to provide a safer health-assurance for the operation staff.

Another object of the present invention is to provide a relocatable container inspection device, which can be run reliably at different environments.

Another object of the present invention is to provide a relocatable container inspection device, which can detect a larger range in the cross-section of the inspected container, so as to be suitable to inspect containers with different dimensions.

Another object of the present invention is to provide a relocatable container inspection device, which can occupy less area in site, and even needs less construction land, so that can lower the cost for construction of the device in site.

TECHNICAL SOLUTIONS OF THE INVENTION

According to the present invention, there is provided a device for inspecting a container, the device comprising: a first cabin unit including a radiation source for generating a beam of penetration radiation for penetrating the container to be inspected; a second cabin unit including detectors for detecting the beam of penetration radiation penetrating through the container being inspected and producing corresponding radiographic signals, the second cabin unit and the first cabin unit being arranged oppositely in both sides of an inspection passage; a gantry unit bridging the first cabin unit and the second cabin unit to form a portal-shaped frame adapted for straddling the container being inspected; means for moving the frame relative to the container being inspected along the inspection passage, so that the detectors receive the beam of the penetration radiation generated from the radiation resource and penetrating through the container being inspected, thereby continuously scanning the container and producing the corresponding radiographic signals, wherein the first cabin unit, the second cabin unit and the gantry unit are all individually made as modular units so as to be quickly and easily assembled and disassembled with each other on the inspection site.

Preferably, the gantry unit includes a horizontal girder and two vertical auxiliary supports disassembly connected to the opposite ends of the horizontal girder at their upper ends and to the first cabin unit and the second cabin unit at their lower ends, respectively.

Preferably, the means for moving the frame comprises running wheels mounted in a rotary manner to the bottoms of the first cabin unit and the second cabin unit, and a driving means for driving the running wheels rotating.

Preferably, the device further comprising rails for guiding the movement of the running wheels thereon.

Preferably, additional detectors for receiving the slanting upwards beam of penetration radiation penetrating through the container being inspected and producing corresponding radiographic signals are respectively provided in the vertical auxiliary supports and in the end portion of the horizontal girder near the second cabin unit.

Preferably, the radiation source is an electron linear accelerator or a radioisotope.

Preferably, further comprising at least one operation cabin unit for controlling the device.

Preferably, the first cabin unit, the second cabin unit, the gantry unit, and the operation cabin unit are sized to be suitable for road transports.

ADVANTAGES OF THE PRESENT INVENTIION

According to the present invention, the device for inspecting a container comprises a modularized unit for accommodating the radiation source, a modularized unit for accommodating the detectors, a modularized gantry unit bridging the modularized unit for accommodating the radiation source and the modularized unit for accommodating the detectors, and at least one modularized unit for accommodating the operation control equipments. Each of the modularized units is provided with positioning and connecting means which is known in the prior art, for connecting to another modularized unit. It is not necessary to use any large or special crane in disassembling or reassembling the modularized units. Therefore, according to the present invention, the relocatable container inspection device with modularized units can be easily assembled and disassembled in the work site. In addition, each modular unit is configured and sized to be suitable for road transports of the ordinary vehicle, thereby facilitating the relocation of the device.

Further, according to the present invention, once the modularized unit for accommodating the radiation source and the modularized unit for accommodating the detectors are put into place, they are not necessary to be further lifted or lowered, so it does not need any complicated lifter. In addition, the operators are not necessary to do any altitude work. Therefore, the device for inspecting a container according to the present invention has a simple structure and is convenient to be operated. Since every equipments are respectively arranged into modularized units and are adjusted into the best working status in advance, the maintaining work in site is kept minimum.

Further, according to the present invention, all of the modularized units are designed to have not too much heavy weight, so that the volume, the thickness and the weight of the beam stop can be increased to enough values as required during the design of the device, thus the dosage of radiation source can be increased in use. As a result, the radiographic image becomes much more clear. Thus, the device according to the present invention has an advantage of a clear radiographic image.

Further, according to the device of the present invention, the operators work in at least one specially made operation cabin unit, where all of the necessary equipments are installed and adjusted to the best working status in advance, especially, air conditioners are installed. Therefore, wherever the device according to the present invention is conveyed and located so as to perform the container inspection, the operators always work in a desired environment which guarantees to get correct inspection results. Moreover, the modularized unit for accommodating the radiation source and the modularized unit for accommodating the detectors are surrounded by the shield walls, and isolated from the modularized unit for operating and controlling the device. As a result, even if the dosage of the radiation source is increased in use, it is not harmful to the operators' healthy.

Further, according to the device of the present invention, the radiation source and the detectors are respectively arranged in different modularized units and adjusted to the best working status in advance. In addition, the modularized unit for accommodating the radiation source and the modularized unit for accommodating the detectors are both air conditioned. Therefore, wherever the device according to the present invention is conveyed and located so as to perform the container inspection, the radiation source and the detectors can always work in a condition of a constant temperature, a constant humidity, and other stable parameters, not being influenced by unsuitable environments in site. That is to say, the device according to the present invention can always work well and run reliably, no matter how bad the ambient condition is.

Further, according to the device of the present invention, the modularized unit for accommodating the radiation source and the modularized unit for accommodating the detectors are both arranged in lower positions in site, so that the radiation source can send out beams for scanning lower positions. On the other hand, additional detectors are also provided in the auxiliary support provided above the modularized unit for accommodating the detectors and in the horizontal girder, so that the radiation source can also send out upward inclined beams so as to scan the top of the container being inspected. Therefore, the device according to the present invention has a wide enough scanning angle, even suitable for the huge container's inspection while it is not necessary to lift or lower the modularized unit for accommodating the radiation source and the modularized unit for accommodating the detectors.

Further, the device according to the present invention is provided with its own power to drive the device to move on, and the horizontal girder is provided above the container being inspected, so that the area necessary for the device to work is reduced. Moreover, according to the device of the present invention, it is only necessary to prepare a dedicated area for the device to be operated. Moreover, it does not need to prepare any other dedicated area around the device as a fix inspection device of the prior art. Therefore, large construction field is prevented, so that the construction cost is also reduced.

As stated above, it is the special structure of the device according to the present invention that makes the radiographic image more clear, makes more cross section be scanned, and makes the scanning equipments run in better condition so that the inspection reliability of the device becomes higher. Moreover, the device according to the present invention also has advantages of occupying a small area for the entire device to be operated, and being capable for more containers to be inspected in a certain time. As the simply-equipped shield walls are adapted, the total investment for the device is reduced, and the construction period becomes shorter. Especially, the entire device can be disassembled and conveyed from one site to another site as well as be settled to work in a limited period. Once settled, the device can be run in a security and reliability manner.

In a word, the relocatable container inspection device with modularized units according to the present invention has the advantages of both the fixed-site container inspection device and the mobile container inspection device, while has overcome the drawbacks of the two kinds of the container inspection devices in the prior art.

As stated above, the present invention has overcome the drawbacks in the prior art, providing a relocatable container inspection device with modularized units, which takes a small area for the entire device to be operated, is easily to be operated, needs less investment, is able to inspect even huge containers and get more clear radiographic image, and is convenient and quick to be disassembled, moved to and reassembled in another inspection site. In use, it is convenient for the device according to the present invention to be moved from one inspection site to another. Moreover, the device can be settled to work with only a short time for reassembling and adjusting.

BRIEF DESCRIPTION OF THE ACCOMPANYING DRAWINGS

Figure 2:
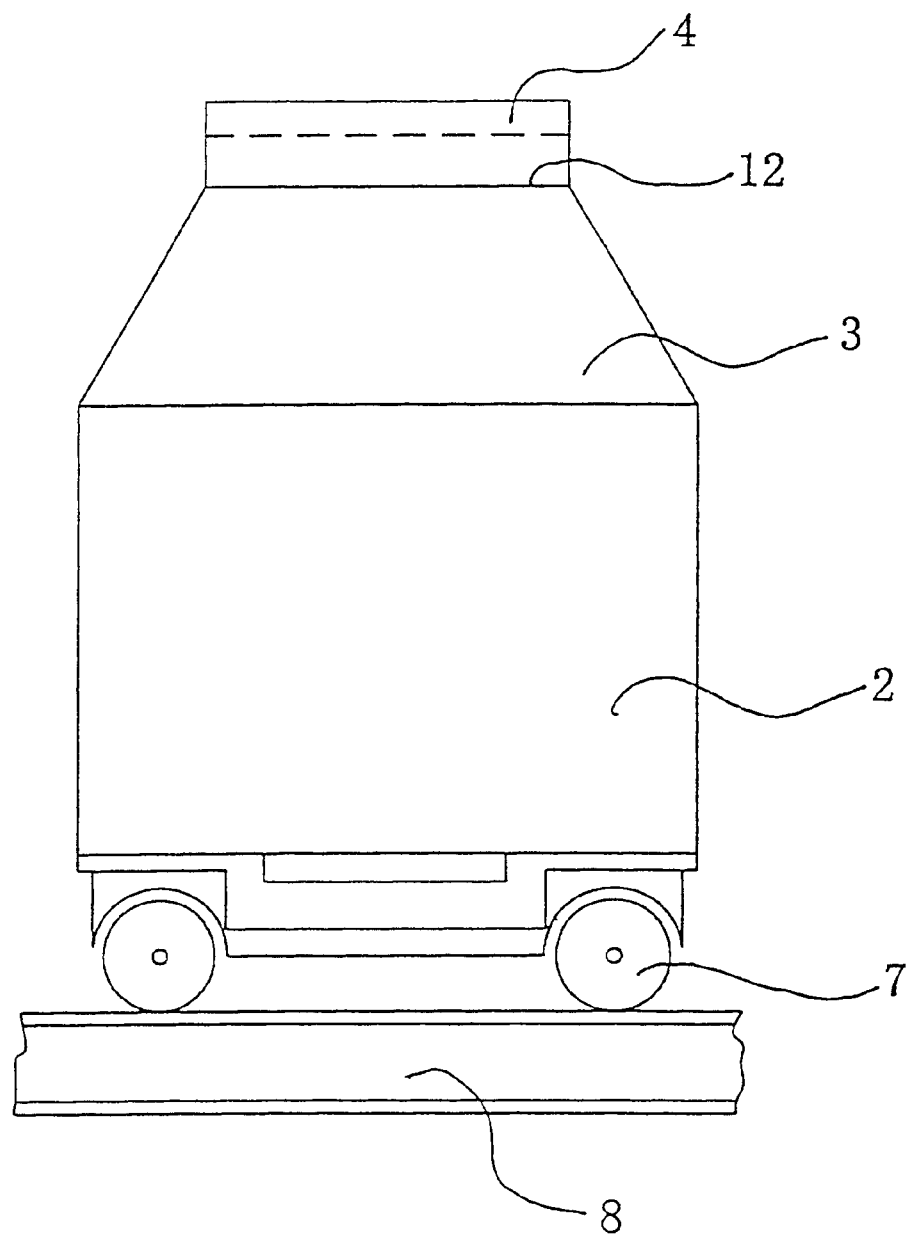

FIG. 1 is a front view of the relocatable container inspection device with modularized units according to the present invention; and FIG. 2 is a side view of the container inspection device with modularized units as shown in FIG. 1.

BEST MODE FOR CARRING OUT THE INVENTION

The invention will be described in detail by reference to the accompanying drawings and the specific embodiments.

As shown in the FIGS. 1 and 2, the relocatable container inspection device with modularized units according to the present invention comprises a radiation source formed as an electron linear accelerator or radioisotope, the detectors and other relevant control equipments. The radiation source is provided into the first cabin unit or a left equipment cabin 2, for generating such as X-ray beams penetrating through the container to be inspected. The detectors 10 are provided into the second cabin unit or a right equipment cabin 6, for receiving the X-ray beams generated from the radiation source and penetrating through the container being inspected, and sending out signals of the image of objects in the container. A left auxiliary support 3 and a right auxiliary support 5 are provided on the top of the left equipment cabin 2 and right equipment cabin 6, respectively. A horizontal girder 4 is provided overhead the top of the auxiliary supports 3, 5 so as to form a gantry unit. Additional detectors 11, 12 are also respectively provided in the right auxiliary support 5 and on the region of horizontal girder 4 close to the right equipment 6, for receiving the inclined and upwards X-ray beams penetrating through the container being inspected. A left running means and a right running means are pivotally mounted on the bottom of the first cabin unit 2 and the second cabin unit 6, respectively. As to the detailed structure of running means, the running wheels 7, 7 are controlled by an AC adjustable speed motor 9 which is in turn controlled by a controlling module, so as to move alone the two sides of an inspection passage, and the running wheels 7, 7 run on the rails 8 which are provided on the ground. Corresponding controlling modules are provided into the left equipment cabin 2, the right equipment cabin 6 and the auxiliary supports 3, 5, as well as the horizontal girder 4, respectively. A portal-shaped frame is formed by assembling the left equipment cabin 2, the right equipment cabin 6 and the auxiliary supports 3, 5 and the horizontal girder 4, and is of 2000 mm~4500 mm in width and 1400 mm~5500 mm in height. These dimensions facilitate the vehicles carried with container to be inspected to pass through the portal-shaped frame. Said vehicles carried with container to be inspected may be cars or even huge container-carrying truck which are available in the world. The X-ray beams generated from the radiation source which is located in the left equipment cabin 2 are oriented to the detectors mounted in the right equipment cabin 6, the right auxiliary support 5, and the horizontal girder 4, respectively. Each of the units mentioned above is designed as an individual module, so that with only simply superimposed connection, the whole inspection device can be quickly established in site.

The operation of the device according to the present invention is as follows. After the inspection device is established as procedures mentioned above, a remote controlling apparatus (operation cabin module) is employed to control the device according to the present invention. By means of control module, the running wheels 7, 7 are driven to run on the two parallel rails 8, so that the portal-shaped frame which is constituted by the left equipment cabin 2, the right equipment cabin 6, the left auxiliary support 3, the right auxiliary support 5 and the horizontal girder 4 moves overhead relatively to the container being inspected, while automatic scanning is performed, and radiographic image data is sent out. The radiographic image of the container being inspected is obtained by the remote controlling apparatus. When it is necessary for the device according to the present invention to be moved to another site to perform the inspection of containers, the device can be disassembled as a procedure from the end to the beginning in the assembling steps. Then, the dismounted modular units can be conveyed by a flatcar to the new site.

It will be appreciated that, as the hints in the embodiment mentioned above, the running wheel 7 could run directly on the ground if the running wheels attached to the bottom of the left and the right running means respectively are made of rubber. In addition, the positions of the left equipment cabin 2, the right equipment cabin 6 and those of other units may also be changed as required. All such variations and modifications are intended to be within the scope of protection of the present invention.

It is noted that the device according to the present invention has several individual modules which can be superimposed and connected to each other so as to establish the device according to the present invention, on the other hand, the complete set of the device according to the present invention can be disassembled into several individual modules. The width and the height of the two equipment cabins and at least one operation cabin are designed to meet the profile dimensions as regulations of road transports, so that the conveyance of the cabins or units by the trucks are not limited by road transporting rules. Therefore, it is feasible to convey every units of the device from one inspection site to another. Moreover, the top and the bottom engagement surfaces of two equipment cabins are integrally machined. Further, the positioning of the units and the connecting of the units with each other are all realized by benefit from the process of one planar support abutting against another and using locating pin to facilitate the precision positioning. Therefore, the device according to the present invention can be assembled together in precision. Thus, the device according to the present invention has advantages of being easy to be machined, being accurate to be positioned, being low cost, and being convenient to be assembled and adjusted. Compared with the fix-site container inspection device in the prior art, the device according to the present invention needs shorter period of manufacture and installation, less investment, and smaller area for operation of the device. Moreover, compared with the mobile container inspection device in the prior art, the device according to the present invention has advantages of being able to scan in a larger range of cross sections of containers, providing more suitable working condition for the scanning equipments of the device, increasing the reliability for the scanning equipments of the device, and getting more clear radiographic image. In consequence, the device according to the present invention can be widely introduced to customs, airport and other anti-smuggling or security inspection places.

Compared with other container inspection devices, the device according to the present invention has advantages of being compact in structure, convenient for operation, less area occupation, and higher efficient for container inspection.

As stated above, the relocatable container inspection device with modularized units according to the present invention has the advantages of both the fixed-site container inspection device and the mobile container inspection device, while overcomes the drawbacks of the two kinds of the container inspection devices in prior art.

Moreover, the radiation source used in the present invention can also be a X-ray tube, a cyclotron, a betatron, an electrostatic accelerator, an X-ray source or a ?-ray source.

According to another embodiment of this invention, the detector provided in the second cabin unit may align up and down with the detector provided in the auxiliary support connected with the second cabin unit. At the same time, the detector provided in the horizontal girder is not necessary provided so as to extend as long as to the right end of the horizontal girder.

As stated above, the present invention has overcome the drawbacks in the prior art, providing a relocatable container inspection device with modularized units, which occupies a small area for the entire device to be operated, is easy to be operated, needs less investment, is able to inspect even huge containers and get much clear radiographic image, and is convenient and quickly to be disassembled, moved to and reassembled in another inspection site. In use, it is convenient for the device according to the present invention to be moved from one inspection site to another. Moreover, the device can be settled to work with only a short time of reassembling and adjusting.

Although the embodiments of the present invention has been explained in detail, it is apparent to those skilled in the art, the described embodiments of the invention are intended to be merely exemplary, and numerous variations and modifications will be available. However, such variations and modifications are all intended to be within the scope of the present invention as defined in the appended claims.

What is claimed is:

1. A device with modularized units for inspecting a container, the device comprising:

a first modular cabin unit (2) within which a radiation source is mounted for generating a beam of penetration radiation for penetrating the container to be inspected;

a second modular cabin unit (6) within which detectors (10) are mounted for detecting the beam of penetration radiation penetrating through the container being inspected and producing corresponding radiographic signals, the second modular cabin unit (6) and the first modular cabin unit (2) being arranged in spaced relationship from each other to define an inspection passage and wherein the first and second modular cabin units (2, 6) are at opposite sides of the inspection passage;

a modular gantry unit (3, 4, 5) joined to and bridging the first modular cabin unit (2) and the second modular cabin unit (6) to form a portal-shaped frame adapted for straddling the container being inspected, and additional detectors (11, 12) being mounted within the modular gantry unit (3, 4, 5);

means for a moving the first and second modular cabin units (2, 6) and the modular gantry unit (3, 4, 5) in unison relative to the container being inspected along the inspection passage, so that the detectors (10, 11, 12) receive the beam of the penetration radiation generated from the radiation source and passing through the container being inspected, thereby continuously scanning the container and producing the corresponding radiographic signals, wherein the first modular cabin unit (2), the second modular cabin unit (6) and the modular gantry unit (3, 4, 5) are each individual modular units that are quickly and easily joined together and separable from each other at an inspection site.

2. The device according to the claim 1, wherein the modular gantry unit (3, 4, 5) includes a horizontal girder (4) and two vertical auxiliary supports (3, 5) having upper and lower ends releasably connected to the opposite ends of the horizontal girder (4) at their upper ends and to the first modular cabin unit (2) and the second modular cabin unit (6) at their lower ends, respectively.

3. The device according to the claim 1, wherein the means for moving the frame comprises running wheels (7, 7)

rotatably mounted to the bottoms of the first modular cabin unit (2) and the second modular cabin unit (6), and a driving means (9) for rotatably moving the running wheels (7, 7).

4. The device according to the claim 3, further comprising rails (8) for guiding the movement of the running wheels (7, 7) thereon.

5. The device according to the claim 2, wherein the additional detectors (11, 12) receive upwardly slanting beams of penetration radiation penetrating through the container being inspected and produce corresponding radiographic signals and are respectively provided in one of the vertical auxiliary supports (5) and in the end portion of the horizontal girder (4) near the second modular cabin unit (6).

6. The device according to the claim 1, wherein the radiation source is an electron linear accelerator or a radioisotope.

7. The device according to the claim 1, further comprising at least one operation cabin unit for controlling the device.

8. The device according to the claim 7, wherein the first modular cabin unit (2), the second modular cabin unit (6), the modular gantry unit (3, 4, 5) and the operation cabin unit are sized to be suitable for road transport.

9. The device according to claim 1, wherein said first modular cabin unit (2) and said second modular cabin unit (6) are air conditioned.

10. The device according to claim 1, wherein each of said first modular cabin unit (2), second modular cabin unit (6) and modular gantry unit (3, 4, 5) is provided with positioning and connecting means for superimposed connection therebetween.

* * * * *